US00PP30270P2

(12) United States Plant Patent
Woods

(10) Patent No.: US PP30,270 P2
(45) Date of Patent: Mar. 5, 2019

(54) ***HIBISCUS* PLANT NAMED 'RWOODS6'**

(50) Latin Name: *Hibiscus syriacus*
Varietal Denomination: RWOODS6

(71) Applicant: Roderick Ian Woods, King's Lynn (GB)

(72) Inventor: Roderick Ian Woods, King's Lynn (GB)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 15/731,934

(22) Filed: Aug. 25, 2017

(51) Int. Cl.
*A01H 5/02* (2018.01)

(52) U.S. Cl.
USPC ..... Plt./257
CPC ..... *A01H 5/02* (2013.01)

(58) Field of Classification Search
USPC ..... Plt./257
See application file for complete search history.

(56) References Cited

PUBLICATIONS

UPOV hit on *Hibiscus* plant named 'RWOODS6', QZ PBR 20163042, filed Dec. 4, 2016.*

* cited by examiner

*Primary Examiner* — Anne Marie Grunberg
(74) *Attorney, Agent, or Firm* — Cassandra Bright

(57) ABSTRACT

A new and distinct cultivar of *Hibiscus* plant named 'RWOODS6' is disclosed, characterized by large, semi-double white flowers with red-purple streaking and basal blotch. Flowers are up to 13 cm in diameter. Flower petals are strong and tolerate wind and rain well. The new variety is a *Hibiscus*, normally produced as an outdoor garden or container plant.

2 Drawing Sheets

Figure 1:
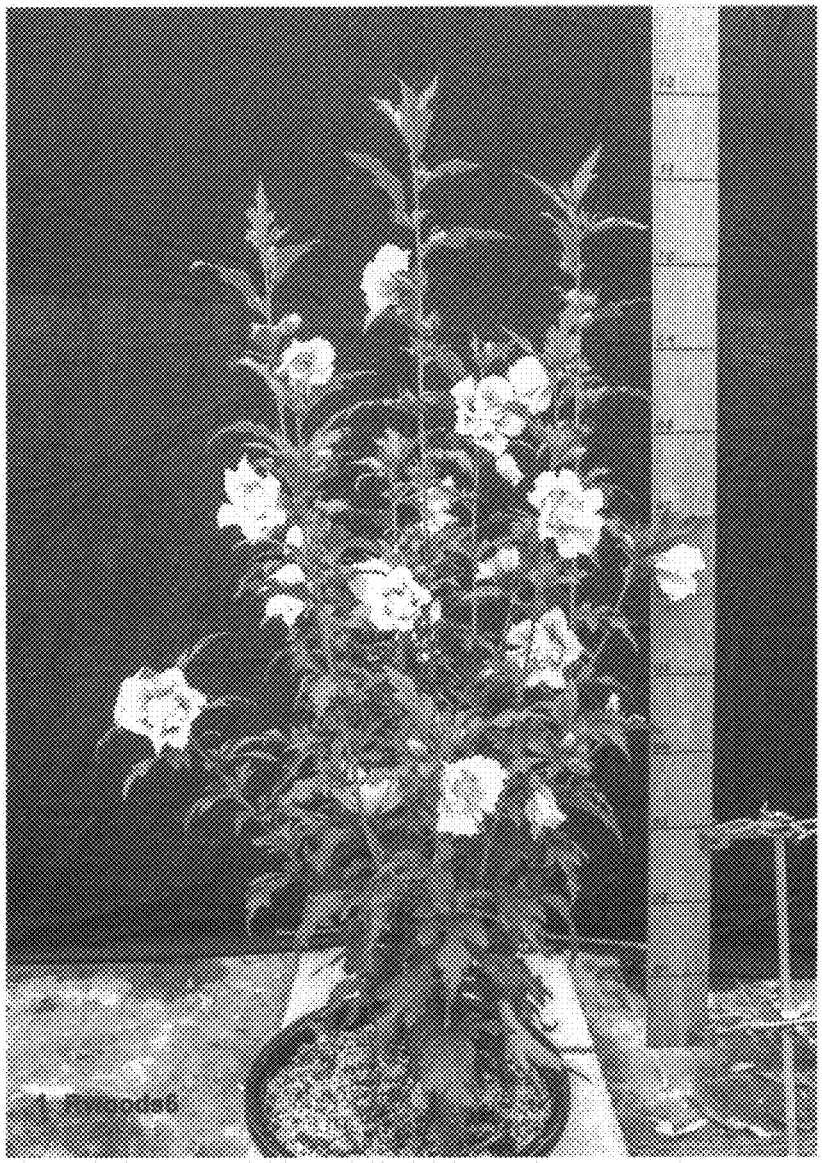

Latin name of the genus and species: *Hibiscus syriacus*. Variety denomination: 'RWOODS6'.

BACKGROUND OF THE INVENTION

The new *Hibiscus* cultivar is a product of a planned breeding program conducted by the inventor, Roderick Ian Woods. The objective of the breeding program was to produce new *Hibiscus syriacus* varieties with double or semi-double flowers on vigorous plants. The cross resulting in this new variety was made during the Summer of 2010.

The seed parent is the unpatented proprietary *Hibiscus syriacus* '9872'. The pollen parent is the unpatented proprietary variety *Hibiscus syriacus* '10672'. The new variety was identified as a potentially interesting selection in October 2010. Selection was made at a research nursery in Norfolk, the United Kingdom.

Asexual reproduction of the new cultivar 'RWOODS6' was first performed in February 2012 in Norfolk, UK. Vegetative soft wood cuttings were grafted onto an unnamed, unpatented *Hibiscus syriacus* rootstock. Subsequent propagation has shown that the unique features of this cultivar are stable and reproduced true to type in 6 successive generations.

SUMMARY OF THE INVENTION

The cultivar 'RWOODS6' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RWOODS6' These characteristics in combination distinguish 'RWOODS6' as a new and distinct *Hibiscus* cultivar:

1. White flowers heavily marked with a red-purple basal patch and red-purple streaks.
2. Flowers with a large central tuft of petaloid staminodes.
3. Strong petals withstanding environmental stressors such as wind and rain.
4. Large flowers with an average diameter of 12 cm and up to 13 cm in diameter.
5. Vigorous plants with good resistance to wet weather.
6. Very few true stamens and very little pollen.

PARENT COMPARISON

Plants of the new cultivar 'RWOODS6' are similar to plants of the seed parent variety in most horticultural characteristics, however, plants of the new cultivar 'RWOODS6' differ in the following;

1. The new variety produces flowers with a full, tufted, staminoidal center, the seed parent produces a very small staminoidal center.
2. Petals of the new variety are much more resistant to damage by wind and rain.

Plants of the new cultivar 'RWOODS6' are similar to plants of the pollen parent in most horticultural characteristics, however, plants of the new cultivar 'RWOODS6' differ in the following;

1. The new variety produces flowers with a full, tufted, staminoidal center, the pollen parent produces a very small staminoidal center.

2. The new variety has a well formed, staminoidal center, the center of the pollen parent is irregularly shaped
3. The new variety produces flowers of approximately 12 cm in diameter, the pollen parent flowers are on average 10 cm in diameter.

COMMERCIAL COMPARISON

Plants of the new cultivar 'RWOODS6' can be compared to the variety *Hibiscus* 'Antong Two', U.S. Plant Pat. No. 19,547. These varieties are similar in most horticultural characteristics however, 'RWOODS6' differs in the following:

1. The new variety produces flowers with a full, tufted, staminoidal center, this comparator produces a single flower.
2. The new variety produces a flower with more red-purple central coloration.

Plants of the new cultivar 'RWOODS6' can be compared to the variety *Hibiscus* 'Notwoodtwo', U.S. Plant Pat. No. 12,612. These varieties are similar in most horticultural characteristics however, 'RWOODS6' differs in the following:

1. The new variety produces flowers with on average 25 percent more petaloids, than this comparator.
2. The new variety produces a white flower with red-purple basal blotch and streaks, this comparator flower is solid white.
3. At maturity, plants of the new variety are slightly smaller than plants of this comparator.
4. Foliage of the new variety is somewhat larger than foliage of this comparator.

Plants of the new cultivar 'RWOODS6' can be compared to the variety *Hibiscus* 'JWNWOOD4', U.S. Plant Pat. No. 24,336. These varieties are similar in most horticultural characteristics however, 'RWOODS6' differs in the following:

1. The new variety produces flowers with on average 25 percent less petaloids, than this comparator.
2. The new variety produces a white flower with red-purple basal blotch and streaks, this comparator produces a pink flower with a red-purple basal blotch and no streaks.
3. At maturity, plants of the new variety are slightly larger than plants of this comparator.
4. Foliage of the new variety is larger than foliage of this comparator.
5. The new variety produces a flower with a diameter up to 13 cm, the largest flower produced by this comparator is typically 9 cm.

BRIEF DESCRIPTION OF THE PHOTOGRAPHS

Figure 2:
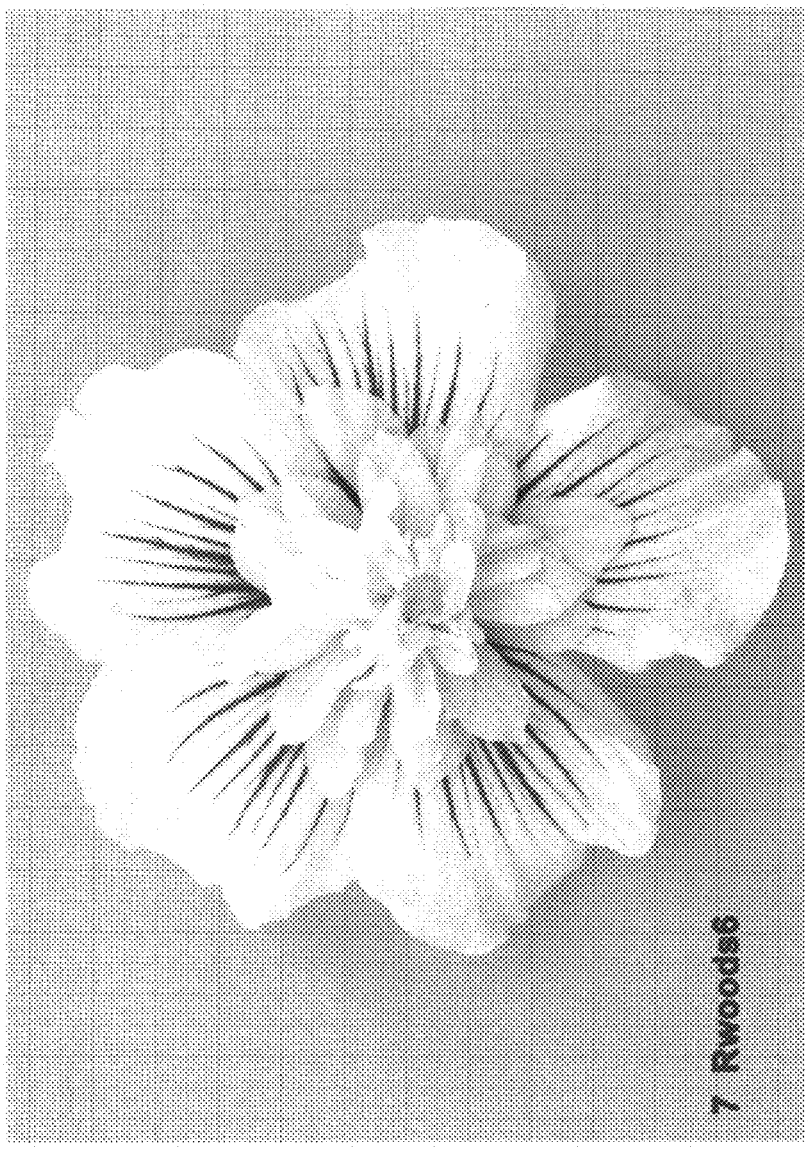

The accompanying photograph in FIG. 1 illustrates in full color a typical plant of 'RWOODS6' grown in an approximately 3 gallon pot, in Norfolk, United Kingdom FIG. 2 illustrates in full color a typical flower of 'RWOODS6'. Age of the plant photographed is approximately 2 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, $6^{th}$ edition, except where general terms of ordinary dictionary significance are used. The following observations and measurements describe plants grown in a polyhouse in Norfolk, UK. Measurements were taken during the July of 2017. The plants were about 2 years old in 2 gallon containers, unless otherwise noted as a mature plant of approximately 5 years. The growing temperature ranged from approximately 18° C. to 27° C. during the day and 5° C. to 10° C. at night. Measurements and numerical values represent averages of typical plant types.

Botanical classification: *Hibiscus syriacus* 'RWOODS6'.

PROPAGATION

Time to initiate roots: 20 days at approximately 25° C.

Root description: Very well branched from initial tap root. Fleshy, becoming woody with age. Fibrous, medium root thickness. Young root tips colored near Yellow-White 158D, mature roots near Greyed-Yellow 161C.

Time to produce a rooted young plant: About 90 days at 25° C.

PLANT

Plant type: Perennial shrub.

Age of plant described: Approximately 2 years old.

Pot size of plant described: 2 gallon pot.

Growth habit: Upright.

Overall plant shape: Narrow inverted triangle when young, becoming an irregular sphere with age.

Height: 2.5 meters at 5 years old, planted in the ground.

Plant spread: 2.0 meters at 5 years old.

Growth rate: Average.

Plant vigor: Strong.

Branching characteristics: Lateral branches grow from leaf axils to create a bushy plant. Cutting or grafted propagations from lateral branches grow multiple upright stems with lateral branches. Overall the plant is freely branching when pinched.

Length of primary lateral branches: 40 to 60 cm.

Diameter of lateral branches: 5 mm.

Quantity of lateral branches: Average 5 in first year from grafting, 10 to 15 in second year after light pruning.

Stem:

*Stem shape.*—Cylindrical.

*Stem strength.*—Strong and flexible.

*Color.*—Stem: Near RHS Greyed-Green 195A. Bark: Near RHS Grey-brown 197B.

*Pubescence.*—Glabrous. When very young slight pubescence.

*Angle of attachment.*—Average angles 40° to 75° from center of plant.

Other: Axillary buds at nodes on strongly growing stems and lateral branches may develop short spurs 1 to 5 mm long producing leaves and a succession of flowers.

FOLIAGE

Leaf:

*Arrangement*.—Typically alternate with initially single leaves per node. Subsequently additional leaves and flower buds develop at each node producing a cluster of leaves of decreasing size each subtending a flower bud or short spur.

*Leaf shape*.—Oval rhombic, tri-lobed.

*Average length*.—10.0 cm on average with a typical range of 8.0 to 15 cm.

*Average width*.—5.5 cm on average with a typical range of 4.5 to 7.5 cm.

*Apex*.—Acute.

*Base*.—Cuneate.

*Margin*.—Tri-lobed and coarsely dentate, with dentations either serrate or crenate.

*Texture of top surface*.—Glabrous.

*Texture of bottom surface*.—Smooth. Main veins and secondary veins with sparse adpressed hairs.

*Color*.—Young foliage upper side: Near RHS Yellow-Green 144B. Young foliage under side: Near RHS Yellow-Green 145A. Mature foliage upper side: Near RHS Green 137A. Mature foliage under side: Yellow-Green, between 146A.

*Venation*.—Pattern: Palmate. Color upper side: Near RHS Yellow-Green 147D. Color under side: Near RHS Yellow-Green 148D.

*Petiole*.—Average Length: 1.7 cm with a typical range of 1.5 to 2.0 cm. Diameter: 1.8 mm. Petiole color upper side: Near RHS Green 137A. Petiole color lower side: Near RHS Yellow-Green 146A. Petiole Texture upper side: Smooth. Petiole Texture lower side: Smooth.

*Stipules*.—Awn shaped stipules at petiole and peduncle bases. Initially Green 137C turning Grey-Brown 199A. 1.0 to 1.5 mm. Quantity varies, average 2 to 5.

FLOWER

Natural flowering season: Mid-July until end of October continuously, in Norfolk, UK.

Flowering form: Semi-double, rotate. One whorl of 5 petals and a tuft of petaloid staminodes in center.

Flower habit: Solitary, emerging from leaf axils.

Flower longevity on plant: About 4 days.

Quantity of flowers per plant: About 350 flowers and buds at once on a mature plant.

Flower shape: Overall shape is a half dome.

Rate of flower opening: Approximately 1 days from bud stage open flower.

Flower aspect: Upright and outward.

Size:

*Diameter*.—12 to 13 cm.

*Depth*.—3.0 cm.

Flower other characteristics:

*Persistence*.—Self-cleaning.

*Fragrance*.—None.

Bud: Described before showing flower color.

*Shape*.—Pointed oval.

*Length*.—Average 2.2 cm.

*Diameter*.—Average 1.2 cm.

*Color*.—Near Yellow-Green 146A.

Petal:

*Petal arrangement*.—Rotate, overlapping.

*Number of petals per flower*.—5 large outer petals.

*Fused*.—No.

*Petal shape*.—Wide rounded deltoid, slightly asymmetric.

*Petal base*.—Adnate to staminal tube.

*Margin*.—Entire.

*Tip shape*.—Irregular, finely repand.

*Length*.—Up to 6.0 cm.

*Width*.—Up to 6.0 cm.

*Texture*.—Upper: Glabrous. Lower: Glabrous, veins raised.

*Appearance*.—Upper surface matte with glossy base. Lower surface matte.

*Aspect*.—Flat to slightly cupped.

Petal color:

*When opening*.—Upper surface: Main surface near White 155C, basal patch near Red-Purple 59C. Streaks near Red-Purple 61A and 61B. Basal patch extends about 2.5 cm, streaks an additional 2.5 cm from edge of patch. Streaks typically extending approximately 75% of length of petal. Lower surface: Main surface near White 155C, basal patch near Red-Purple 65D. No streaks.

*Fully opened*.—Upper surface: Main surface near White 155C, basal patch near Red-Purple 59C. Streaks near Red-Purple 61A and 61B. Basal patch extends about 2.5 cm, streaks an additional 2.5 cm from edge of patch. Streaks typically extending approximately 75% of length of petal. Lower surface: Main surface near White 155C, basal patch near Red-Purple 65D. No streaks.

*Fading to*.—Upper surface: Main surface near White 155C, basal patch near Red-Purple 59C. Streaks near Red-Purple 61A and 61B. Basal patch extends about 2.5 cm, streaks an additional 2.5 cm from edge of patch. Streaks typically extending approximately 75% of length of petal. Lower surface: Main surface near White 155C, basal patch near Red-Purple 65D. No streaks.

Petaloids:

*Arrangement*.—Thick central whorl of petaloids.

*Number of petaloids per flower*.—Average 47.

*Shape*.—Obovate.

*Aspect*.—Flat of fluted. Irregular.

*Base*.—Cuneate, attached to stamen filament.

*Margin*.—Entire.

*Tip shape*.—Obtuse or acuminate.

*Length*.—4 mm to 30 mm.

*Width*.—3 mm to 15 mm.

*Texture*.—Upper: Glabrous. Lower: Glabrous.

*Appearance*.—Upper surface matte with glossy base. Lower surface matte.

Petaloid color:

*When opening*.—Upper surface: Near White 155C, tinted Red-Purple 69D. Faint central stripes near Purple 76D. Lower surface: Near White 155C, tinted Red-Purple 69D.

*Fully opened*.—Upper surface: Near White 155C, tinted Red-Purple 69D. Lower surface: Near White 155C, tinted Red-Purple 69D.

Calyx

*Shape*.—Campanulate cup terminating in the acute free sepal tips. The cup is roughly half the length of the calyx. The calyx is surrounded by 5 or rarely up to 8 strap shaped green bracts, making up the epicalyx.

*Length*.—About 2.2 cm.

*Diameter*.—About 1.6 cm.

Sepals:

*Arrangement*.—Rotate, lower 50% fused.

*Number*.—Average 5.

*Shape*.—Narrow deltate.

*Tip*.—Acute.

*Base*.—Fused.

*Margin*.—Entire.

*Length*.—About 1 cm.

*Width*.—About 0.9 cm.

*Texture, upper*.—Glabrous.

*Texture, lower*.—Glabrous, rugose.

*Color*.—Upper surface: Yellow-Green 146A. Under surface: Yellow-Green 146A.

Epicalyx bracts:

*Epicalyx diameter*.—Average 1.7 cm.

*Epicalyx length*.—Average 2.4 cm.

*Quantity of bracts*.—Average 5 or rarely 8.

*Shape*.—Linear.

*Length*.—Average 1.1 cm.

*Width*.—Average 2.0 mm.

*Margin*.—Entire.

*Apex*.—Broad acute.

*Base*.—Fused.

*Texture, upper*.—Glabrous.

*Texture, lower*.—Glabrous, rugose.

*Color*.—Upper surface near Green 137A, lower surface near 137A.

Peduncle:

*Length*.—Average 1.0 cm.

*Diameter*.—3.0 mm.

*Color*.—Near RHS Yellow-Green 146A.

*Orientation*.—About 90°, horizontal to stem.

*Strength*.—Rigid.

*Texture*.—Glabrous, ridged.

REPRODUCTIVE ORGANS

Stamens:

*Number*.—Average 6, clustered and implanted in style, typical of *Hibiscus*.

*Filament length*.—2.0 mm.

*Filament color*.—Near RHS White 155C.

Anthers:

*Shape*.—Reniform when immature, irregular spherical at dehiscence.

*Length*.—2 mm.

*Diameter*.—2 mm.

*Color*.—Near RHS Yellow-Orange 18D.

*Pollen color*.—Near RHS Yellow-Orange 18D.

*Pollen amount*.—Scant.

Pistil:

*Number*.—1.

*Length*.—3.7 cm.

*Style*.—Length: 3.0 cm. Color: Near RHS White 155C.

*Stigma*.—Shape: Rounded cap. Color: Near RHS Green-White 157C.

*Ovary color*.—Near RHS Yellow-Green 145C.

OTHER CHARACTERISTICS

Seeds and fruits: Fruits: Capsule. 3.0 long, 1.5 cm in diameter. Colored near Grey-Brown 199B. About 10 capsules per branch at maturity. Capsule usually empty.

Seed: Typically no seed. If produced 1 to 5 spherical seeds per capsule. About 3 mm long, 3 mm diameter colored near Greyed-Orange 165A.

Disease/pest resistance: Neither resistance nor susceptibility to normal diseases and pests of *Hibiscus syriacus* have been observed.

Garden performance: Good tolerance, performs well in humid conditions.

Temperature tolerance: Low temperature tolerance to at least USDA zone 4, high temperature tolerance to at least 40° C.

What is claimed is:

1. A new and distinct cultivar of *Hibiscus* plant named 'RWOODS6' as herein illustrated and described.

* * * * *